US00PP36220P2

(12) United States Plant Patent
Knoblauch

(10) Patent No.: US PP36,220 P2
(45) Date of Patent: Oct. 22, 2024

(54) ***BEGONIA* PLANT NAMED 'BEYZ0001'**

(50) Latin Name: *Begonia hybrida*
Varietal Denomination: BEYZ0001

(71) Applicant: SYNGENTA CROP PROTECTION AG, Basel (CH)

(72) Inventor: Cathy Knoblauch, Whitecourt (CA)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/445,768

(22) Filed: Jan. 25, 2024

(51) Int. Cl.
*A01H 5/02* (2018.01)
*A01H 6/18* (2018.01)

(52) U.S. Cl.
USPC ..... Plt./343
CPC ..... *A01H 6/185* (2018.05)

(58) Field of Classification Search
USPC ..... Plt./343
CPC ..... A01H 6/185; A01H 5/02
See application file for complete search history.

*Primary Examiner* — Keith O. Robinson
(74) *Attorney, Agent, or Firm* — Dale Skalla

(57) ABSTRACT

A new *Begonia* plant named 'BEYZ0001' particularly distinguished by its rounded, compact and symmetrical habit, double flowers that are soft deep pink in color with very dark mahogany glossy foliage. 'BEYZ0001' blooms continually from early spring onward and has freely produced basal and lateral branching.

1 Drawing Sheet

Latin name of the genus and species of the plant claimed: *Begonia hybrida.*
Varietal denomination: 'BEYZ0001'.

BACKGROUND OF THE NEW PLANT

The present invention comprises a new *Begonia* plant, botanically known as *Begonia hybrida* and hereinafter referred to by the variety name 'BEYZ0001'. 'BEYZ0001' is a product of a planned breeding program in Whitecourt, Alberta Canada. The new cultivar 'BEYZ0001' has rounded, compact and symmetrical habit, double flowers that are soft deep pink in color with very dark mahogany glossy foliage. 'BEYZ0001' blooms continually from early spring onward and has freely produced basal and lateral branching.

The new *Begonia* cultivar, 'BEYZ0001', is the result of a planned pollination and was made in Whitecourt, Alberta, Canada at the inventor's nursery in the month of August 2018.

The female parent of the new cultivar is the unnamed pink *Begonia* seedling, not patented, characterized by its larger flowers and leaves. 'BEYZ0001' differs from the female parent by having a smaller flower. The male parent of the new cultivar is an unnamed, unpatented seedling of the inventor's internal lines, having a smaller white flower and many lateral branches with smaller overall size than 'BEYZ0001'.

The resulting seed was sown in Whitecourt, Alberta, Canada in a controlled greenhouse environment in 2018 and 'BEYZ0001' was selected as one flowering plant within the progeny of the stated cross in 2019.

The first act of asexual reproduction of 'BEYZ0001' was accomplished when vegetative stem cuttings were propagated from the initial selection in May 2019 in Whitecourt, Alberta, Canada.

BRIEF SUMMARY OF INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

A Plant Breeder's Right for this cultivar has not yet been applied for. 'BEYZ0001' has not been made publicly available prior to the effective filing date of this application, notwithstanding any disclosure that may have been made less than one year prior to the effective filing date of this application by the inventor or another who obtained directly from the inventor.

The following traits have been repeatedly observed and are determined to be basic characteristics of the new variety. The combination of these characteristics distinguishes this *Begonia* as a new and distinct variety.

BRIEF DESCRIPTION OF THE PHOTOGRAPHS

The accompanying photographic drawings show typical flower and foliage characteristics of 'BEYZ0001' with colors being as true as possible with an illustration of this type.

Figure 1:
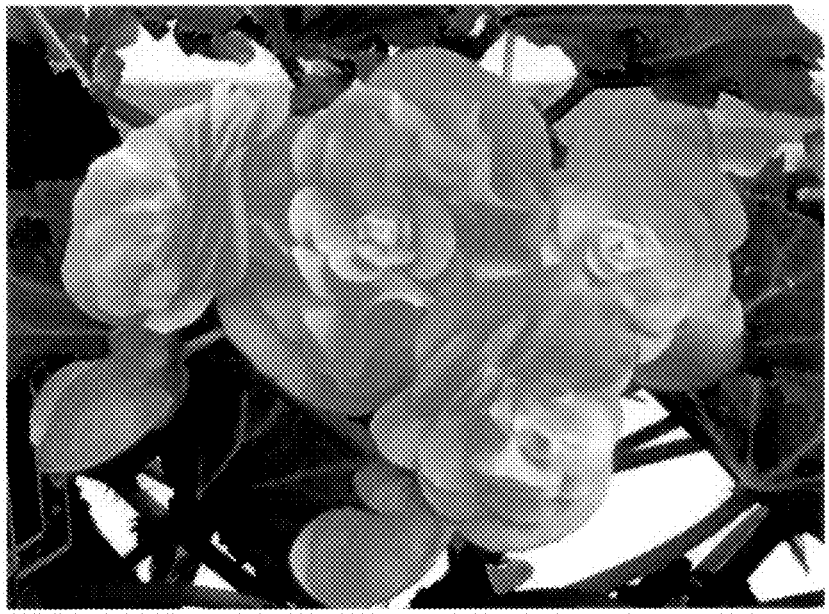
Figure 2:
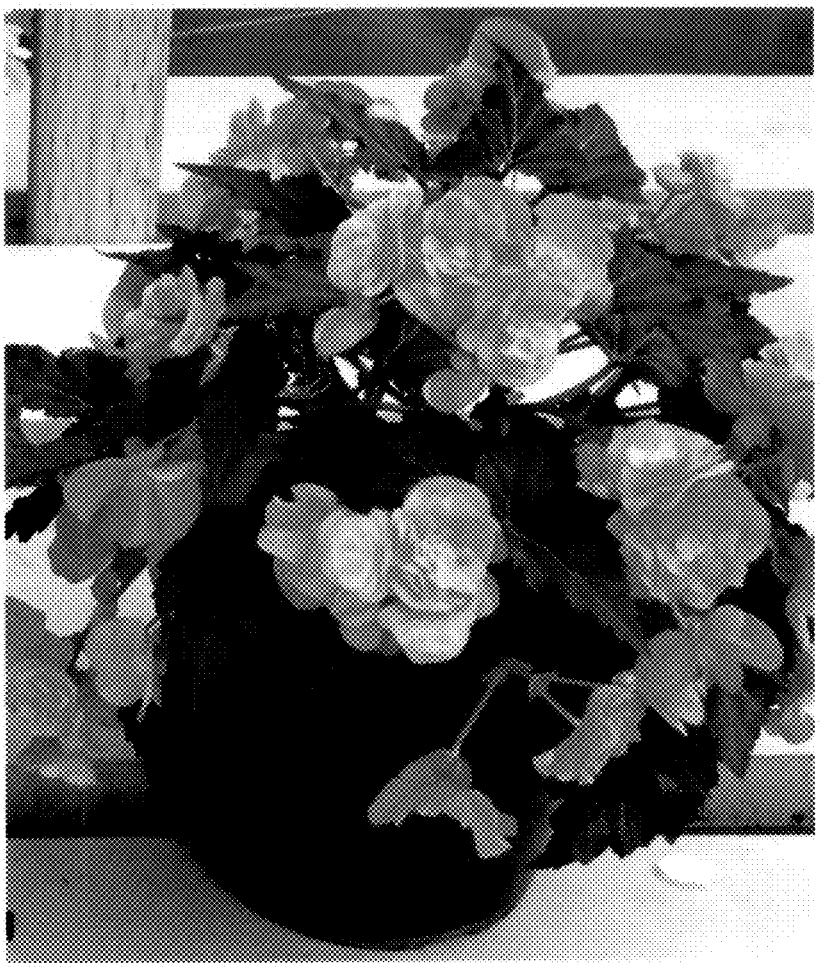

The photographic drawings show in FIG. 1 a close view of an inflorescence taken in Whitecourt, Alberta, Canada in September 2019 and in FIG. 2 a whole flowering plant taken in Whitecourt, Alberta, Canada in September 2019. The age of the plants depicted in FIG. 1 and FIG. 2 are 24 weeks old.

DETAILED BOTANICAL DESCRIPTION

The plant descriptions and measurements were taken in 2023 in Whitecourt, Alberta, Canada. The plants were approximately 6 months old and were growing in 8 inch pots, one plant per pot, in a greenhouse.

Color references are made to The Royal Horticultural Society Colour Chart (R.H.S.) 2001.

TABLE 1

DIFFERENCES BETWEEN THE NEW VARIETY 'BEYZ0001' AND A MOST SIMILAR VARIETY

| | 'BEYZ0001' | 'MOCHA PINK', Not patented |
|---|---|---|
| Flower size: | Smaller | Larger |
| Leaf size: | Smaller | Larger |
| Foliage: | Glabrous | Pubescent |

TRAITS

1. 'BEYZ0001' exhibits a compact symmetrical rounded habit.
2. 'BEYZ0001' has a height of 25 cm and a diameter of 25 cm during one growing season in a one gallon pot.
3. 'BEYZ0001' blooms continuously from spring until fall.
4. 'BEYZ0001' exhibits freely produced basal and lateral branching.
5. 'BEYZ0001' exhibits an upper leaf color close to RHS 200B Propagation:
- *Type*.—Vegetative tip cuttings.
- *Time to initiate roots, summer and winter*.—Spring: 15 days, Winter: 20 days.
- *Time to produce a rooted young plant, summer*.—25-30 days.
- *Time to produce a rooted young plant, winter*.—35-40 days.
- *Root description*.—Medium, thin.
- *Rooting habit*.—Moderately freely branching.

Plant description:
- *Plant and growth habit*.—Upright mounded, freely branched.
- *Plant height, soil level to top of foliar plane*.—20 cm.
- *Plant height, soil level to top of floral plane*.—25 cm.
- *Plant width*.—25-30 cm.
- *Lateral branch description*.—Upright, freely branched.
- *Length*.—Averages 14-16 cm.
- *Diameter*.—Averages 7 mm.
- *Internode length*.—About 2-3 cm.
- *Strength*.—Moderately strong, wiry.
- *Aspect*.—Symmetrical.
- *Texture and luster*.—Smooth, glossy.
- *Color, developing*.—RHS 177A to RHS 179B.
- *Color, developed*.—RHS 199A to RHS 201B.

Leaf description:
- *Color, upper surface*.—Nearest RHS 200B.
- *Color, lower surface*.—Nearest RHS 176B.
- *Arrangement*.—Alternate.
- *Length*.—About 9 cm.
- *Width*.—About 5 cm.
- *Shape*.—Cordate, asymmetrical.
- *Apex*.—Acuminate.
- *Base*.—Cordate.
- *Margin*.—Irregularly dentate.
- *Texture and luster, upper and lower surfaces*.—Upper: Smooth, Glossy. Lower: Sparsely pubescent, smooth, glossy.
- *Developing leaves, upper surface*.—Nearest RHS 200B.
- *Developing leaves, lower surface*.—Nearest RHS 176B.
- *Developed leaves, upper surface*.—Nearest RHS 200B.
- *Developed leaves, lower surface*.—Nearest RHS 176B.
- *Venation pattern*.—Palmate.
- *Developing leaves, upper surface*.—Palmate.
- *Developing leaves, lower surface*.—Palmate.
- *Fully expanded leaves, upper surface*.—Palmate.
- *Fully expanded leaves, lower surface*.—Palmate.

Petioles:
- *Length*.—Average 5-8 cm.
- *Diameter*.—About 2 mm.
- *Texture and luster, upper and lower surfaces*.—Sparsely pubescent with simple colorless hairs.
- *Strength*.—Moderate to strong.
- *Color, upper surface*.—RHS 183D.
- *Color, lower surface*.—RHS 183A.

Stipules:
- *Quantity per leaf*.—2.
- *Length*.—1 cm.
- *Width*.—8 mm.
- *Shape*.—Triangular.
- *Apex*.—Sharply acute.
- *Base*.—Truncate.
- *Margins*.—Ciliate.
- *Color, upper and lower surfaces*.—Upper: RHS 145C, lower: RHS 145D.

Flower description:
- *Flowering habit*.—Continuous.
- *Fragrance*.—None.
- *Natural flowering season*.—Spring and summer.
- *Flower longevity*.—About 30 days.
- *Inflorescence height (including peduncle)*.—About 9 cm.
- *Flower buds, female flowers*.—
- *Length*.—About 5 cm.
- *Diameter, flattened*.—About 4 cm.
- *Shape*.—Obovate.
- *Texture and luster*.—Smooth. Matte.
- *Color, upper surface*.—About RHS 51D.
- *Color, lower surface*.—About RHS 51D.

Tepals:
- *Quantity per flower and arrangement*.—5 in a single whorl.
- *Length, inner tepals*.—None.
- *Length, outer tepals*.—About 2 cm.
- *Width, inner tepals*.—None.
- *Width, outer tepals*.—About 2.5 cm.
- *Shape, inner tepals*.—None.
- *Shape, outer tepals*.—Broadly ovate.
- *Apex, inner tepals*.—None.
- *Apex, outer tepals*.—Ovate.
- *Base, inner and outer tepals*.—Broadly obovate.
- *Margin, inner and outer tepals*.—Entire.
- *Texture and luster, inner and outer tepals, upper surface*.—Smooth, matte.
- *Texture and luster, inner and outer tepals, lower surface*.—Smooth, matte.
- *Color, inner tepals*.—
- *When opening, upper surface*.—None.
- *When opening, lower surface*.—None.
- *Fully opened, upper surface*.—None.
- *Fully opened, lower surface*.—None.
- *Color, outer tepals*.—
- *When opening, upper surface*.—Ranging from RHS 51D to RHS 54D.
- *When opening, lower surface*.—Ranging from RHS 51D to RHS 54D.

*Fully opened, upper surface*.—About RHS 55C.
*Fully opened, lower surface*.—About RHS 55C.
*Tepaloids*.—None observed in female flowers.
*Male flowers*.—
*Size*.—About 4 cm.
*Depth*.—About 5 cm.

Female flowers:
*Size*.—About 4-5 cm width, About 4 cm length.
*Quantity per flower and arrangement*.—5 in a single whorl.
*Length, tepals*.—About 2.5 cm.
*Width, tepals*.—About 3 cm.
*Shape, tepals*.—Broadly ovate.
*Apex, tepals*.—Ovate.
*Base, tepals*.—Obovate.
*Margin, tepals*.—Entire.
*Texture and luster, tepals*.—Smooth, matte.
*When opening, lower surface*.—Smooth, matte.
*When opening, upper surface*.—Smooth, matte.
*Fully opened, upper surface*.—Smooth, matte.
*Fully opened, lower surface*.—Smooth, matte.
*Color, tepals*.—
*When opening, upper surface*.—Ranging from RHS 51D to RHS 54D.
*When opening, lower surface*.—Ranging from RHS 51D to RHS 54D.
*Fully opened, upper and lower surfaces*.—About RHS 55C.
*Tepaloids*.—None observed in female flowers.
*Pedicels*.—
*Length*.—About 2 cm.
*Diameter*.—About 2 mm.
*Angle*.—Mostly upright.
*Strength*.—Moderately strong, wiry.
*Texture and luster*.—Smooth, matte.
*Color, upper surface*.—About RHS 176A.
*Color, lower surface*.—About RHS 177B.
*Reproductive organs, female*.—
*Gynoecium*.—
*Quantity per flower*.—One.
*Pistil length*.—2 mm.
*Stigma diameter*.—5 mm.
*Stigma shape*.—Bifurcated, loose spiral.
*Stigma color*.—Ranging from RHS 11A to RHS 12B.
*Style length*.—1-2 mm.
*Style color*.—RHS 145D.
*Ovary color*.—RHS 145B.
*Seeds and fruits*.—None observed to date.

Male flowers:
*Size, width*.—About 4 cm.
*Size, length*.—About 5 cm.
*Flower buds*.—
*Length*.—About 2 cm.
*Diameter, flattened*.—About 2.5 cm.
*Shape*.—Broadly ovate.
*Texture and luster*.—Smooth, matte.
*Color, upper surface*.—About RHS 51D.
*Color, lower surface*.—About RHS 51D.

Tepals, male flowers:
*Quantity per flower and arrangement*.—About 25 in about 4 whorls.
*Length, inner tepals*.—About 2 cm.
*Length, outer tepals*.—About 3 cm.
*Width, inner tepals*.—About 2 cm.
*Width, outer tepals*.—About 3 cm.
*Shape, inner tepals*.—Broadly obovate.
*Shape, outer tepals*.—Obovate.
*Apex, inner and outer tepals*.—Broadly obovate.
*Base, inner and outer tepals*.—Roundly obtuse.
*Margin, inner and outer tepals*.—Entire.
*Texture and luster, inner and outer tepals, upper surface*.—Smooth, matte.
*Texture and luster, inner and outer tepals, lower surface*.—Smooth, matte.
*Color, inner tepals*.—
*When opening, upper surface*.—Ranging from RHS 50D to RHS 52D.
*When opening, lower surface*.—Ranging from RHS 50D to RHS 52D.
*Fully opened, upper and lower surfaces*.—Ranging from RHS 50D to RHS 52D.
*Color, outer tepals*.—
*When opening, upper surface*.—Ranging from RHS 50D to RHS 52D.
*When opening, lower surface*.—Ranging from RHS 50D to RHS 52D.
*Fully opened, upper surface*.—Ranging from RHS 50D to RHS 52D.
*Fully opened, lower surface*.—Ranging from RHS 50D to RHS 52D.
*Tepaloids*.—10-25 arranged in about 4 whorls.

Peduncles:
*Length*.—About 4 cm.
*Diameter*.—About 3 mm.
*Angle*.—Mostly upright.
*Strength*.—Moderately strong, wiry.
*Texture and luster*.—Smooth, matte.
*Color, upper and lower surfaces*.—Ranging from RHS 177B to RHS 178C.

Pedicels, male flowers:
*Length*.—About 2 cm.
*Diameter*.—About 2 mm.
*Angle*.—Mostly upright.
*Strength*.—Moderately strong, wiry.
*Texture and luster*.—Smooth, matte.
*Color, upper surface*.—About RHS 176A.
*Color, lower surface*.—About RHS 177B.

Flower bracts:
*Quantity per flower and arrangement*.—2, opposite.
*Length*.—About 8 mm.
*Width*.—About 8 mm.
*Shape*.—Broadly ovate.
*Apex*.—Roundly obtuse.
*Base*.—Obtuse.
*Margin*.—Denticulate.
*Texture and luster, upper and lower surfaces*.—Smooth, semi gloss.
*Color, upper and lower surfaces*.—About RHS 138C.

Reproductive organs:
*Androecium*.—
*Stamen quantity per flower*.—None observed, stamens are transformed into tepaloids.
*Filament length*.—None observed.
*Filament color*.—None.
*Anther size*.—None.
*Anther shape*.—None.
*Anther color*.—None.
*Amount of pollen*.—None.
*Pollen color*.—None.

Pathogen & pest resistance: To date, resistance to pathogens and pests common to *Begonia* plants has not been observed on plants of the new *Begonia*.

Temperature tolerance: Plants of the new *Begonia* have been observed to tolerate high temperatures of about 35° C. and to be suitable for USDA Hardiness Zones 7 to 9.

What is claimed is:

1. A new and distinct variety of *Begonia* plant named 'BEYZ0001' substantially as illustrated and described herein.

* * * * *